United States Patent [19]

Kimura

[11] Patent Number: 4,941,828
[45] Date of Patent: Jul. 17, 1990

[54] DENTAL CHUCKLESS HANDPIECE
[75] Inventor: Hiroshi Kimura, Ibaragi, Japan
[73] Assignee: G-C Dental Industrial Corp., Tokyo, Japan
[21] Appl. No.: 213,925
[22] Filed: Jun. 30, 1988
[30] Foreign Application Priority Data Jul. 22, 1987 [JP] Japan .................... 62-181137

[51] Int. Cl.⁵ .................................................. A61C 1/10
[52] U.S. Cl. .................................... 433/114; 433/132; 433/126
[58] Field of Search ............... 433/114, 131, 132, 133, 433/124, 126, 165, 166, 225; 40/913

[56] References Cited

U.S. PATENT DOCUMENTS

| 2,176,698 | 10/1939 | Albrecht | 40/913 |
| 3,955,284 | 5/1976 | Balson | 433/126 |
| 4,004,344 | 1/1977 | Gold et al. | 433/133 |
| 4,231,739 | 11/1980 | Iudica | 433/126 |
| 4,285,671 | 8/1981 | Lustig et al. | 433/133 |
| 4,564,354 | 1/1986 | Rosenstatter | 433/165 |
| 4,759,715 | 7/1988 | Weissman | 433/225 |

*Primary Examiner*—John J. Wilson
*Attorney, Agent, or Firm*—Oblon, Spivak, McClelland, Maier & Neustadt

[57] ABSTRACT

A dental chuckless handpiece of the compressed air drive type includes a body having a head in which bearings are attached to the upper and lower portions of a shaft provided with a turbine impeller, and a rotary member fixedly provided to the lower end of the shaft is mounted in place through the upper and lower bearings. At least portions of the body excepting the head is formed of a synthetic resin discriminably colored with a color including transparent color.

6 Claims, 3 Drawing Sheets

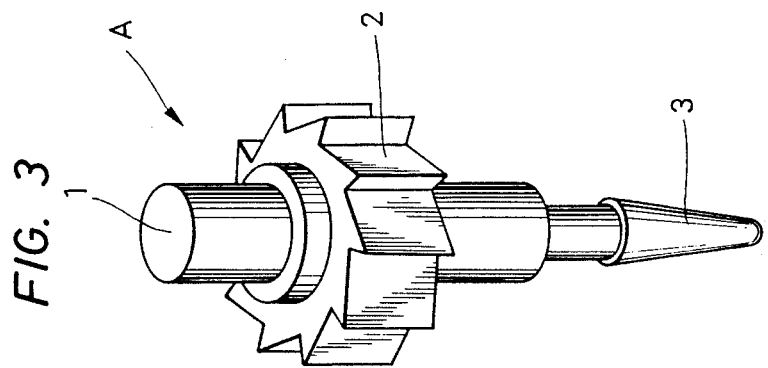
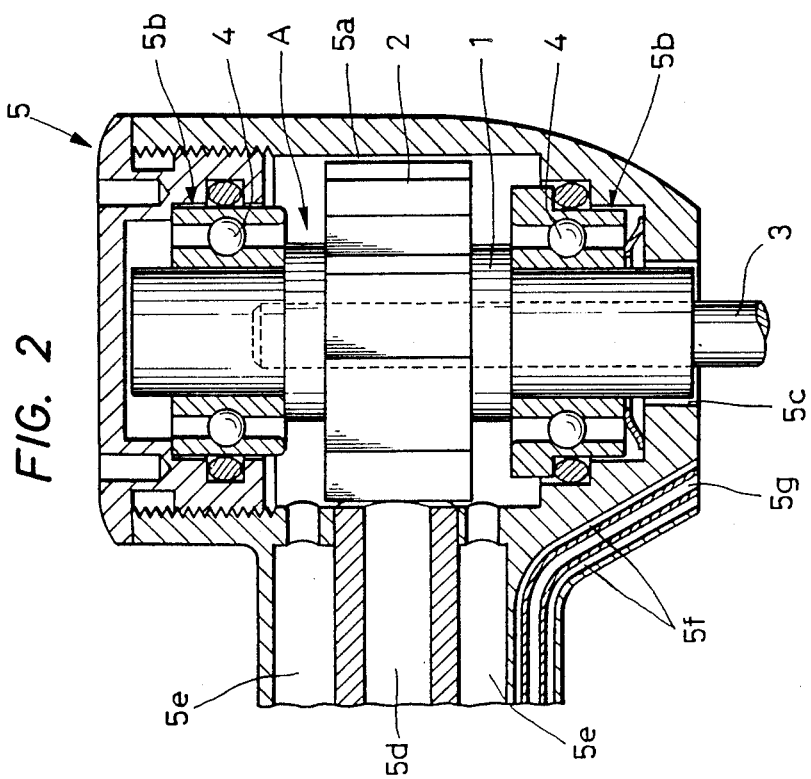

DENTAL CHUCKLESS HANDPIECE

BACKGROUND OF THE INVENTION

1. Field of the Invention

The present invention relates to a dental chuckless handpiece of the compressed air drive type driven at high speeds, and having an integral structure. Rotary member A which is the most important component of the compressed air drive type dental chuckless handpiece, comprises a shaft having a turbine impeller, a grinding tool fixed to the lower end of the shaft and bearings attached above and below the turbine impeller, which generate and maintain a high-speed rotation even under load, whereby the number of the components involved is reduced to a minimum to achieve reductions in the production cost, and whereby any chuck for the fixation of the cutting tool is dispensed with to achieve improvements in manipulability. The present invention is also concerned with a dental chuckless handpiece of the compressed air drive type, which is of the structure that at least the portions of a handpiece body except its head are formed of a synthetic resin to reduce the weight thereof and discriminably colored with a color including transparent color to afford discriminability thereto.

2. Statement of the Prior Art

In general, because the compressed air drive type dental handpiece driven at high speeds is of the structure that bearings are provided so as to securely and pivotably support a rotary shaft in the head of a handpiece body, it is as a whole formed of brass or stainless steel. This handpiece is also of the structure that, for use, a suitable cutting tool, which dentists or dental technicians wish to employ depending upon the intended purpose or use, is held in a chuck portion formed in a rotary member mounted in the head of a handpiece body.

Thus, because the prior art dental handpiece is of the structure that allows free replacement of cutting tools, the chuck portion is formed in the rotary member mounted in the head of the handpiece body. This leads to an increase in the size of the head, which offers a problem in the observation of the given regions of the teeth or dentures to be ground. Another problem also arises in that the operation of holding the cutting tool stably in the chuck portion is troublesome and difficulty is encountered in maintaining the cutting tool in a stable rotating state free from running-out or co-oscillation. There is also a fear that insufficient chucking may cause disconnection of the cutting tool during cutting, resulting in the patient being injured. Still other problems arise in that the prior art handpiece extremely fatigues the operator who uses it for an extended period, since it is so heavy because of the fact that the whole handpiece is formed of brass or stainless steel, and that noise is generated due to leakage of compressed air out of a hole formed in the head for clamping the chuck.

SUMMARY OF THE INVENTION

The present inventors have made various studies to solve the aforesaid problems. In consequence thereof, it has been found that the problems in the observation of the given regions of the teeth or dentures to be ground due to the provision of the chuck, the problems encountered in holding the cutting tool stably in the chuck portion, and the difficulty involved in maintaining the cutting tool in a stable rotating state free from running-out or co-oscillation can be solved by adopting the structure that, of the rotary components driven by compressed air, the cutting tool is integrally provided on a shaft including a turbine impeller other than bearings inevitable to stably rotate the cutting tool even at high speed under load; noise can be reduced by dispensing with the hole for clamping the chuck which is one factor in the generation of noise; the problem that the handpiece body itself is heavy can be solved by forming at least the portions of the handpiece body except its head of a synthetic resin; and the difficulty is discriminating of the cutting tool fixed to the rotary member due to the fact that replacement of the cutting tool is not easy or unfeasible because the aforesaid integral rotary member having the bearings attached to its upper and lower portions are mounted in the head can be eliminated by coloring at least the portions in a color including transparent color for the purpose of corresponding the type of cutting tool to that color in one-match-one relation. Thus, the present inventors have successfully accomplished the present invention.

More specifically, according to one aspect of the present invention (which hereafter is called the first invention), there is provided a dental chuckless handpiece of the compressed air drive type, including a body having a head in which bearings are attached to the upper and lower portions of a shaft provided with a turbine impeller, and a rotary member having a cutting tool fixedly provided to the lower end of the shaft is mounted in place through the upper and lower bearings.

According to another aspect of the present invention (which hereafter is called the second invention), there is provided a dental chuckless handpiece of the compressed air drive type, including a body having a head in which bearings are attached to the upper and lower portions of a shaft provided with a turbine impeller, and a rotary member having a cutting tool fixedly provided to the lower end of the shaft is mounted in place through the upper and lower bearings; at least the portions of said body except said body is formed of a synthetic resin discriminably colored in a color including transparent color.

BRIEF DESCRIPTION OF THE DRAWINGS

The dental chuckless handpiece according to the present invention will now be explained with reference to the embodiments illustrated in the accompanying drawings, which are given for the purpose of illustration alone, and in which:

FIG. 2 is a longitudinally sectioned view illustrating the rotary member which is mounted in the head of the dental chuckless handpiece according to the present invention, FIG. 3 is a perspective view illustrating one embodiment of the rotary member which is used with the dental chuckless handpiece according to the present invention, but to which bearings are not yet attached.

DETAILED DESCRIPTION OF PREFERRED EMBODIMENTS OF THE INVENTION

Figure 1:
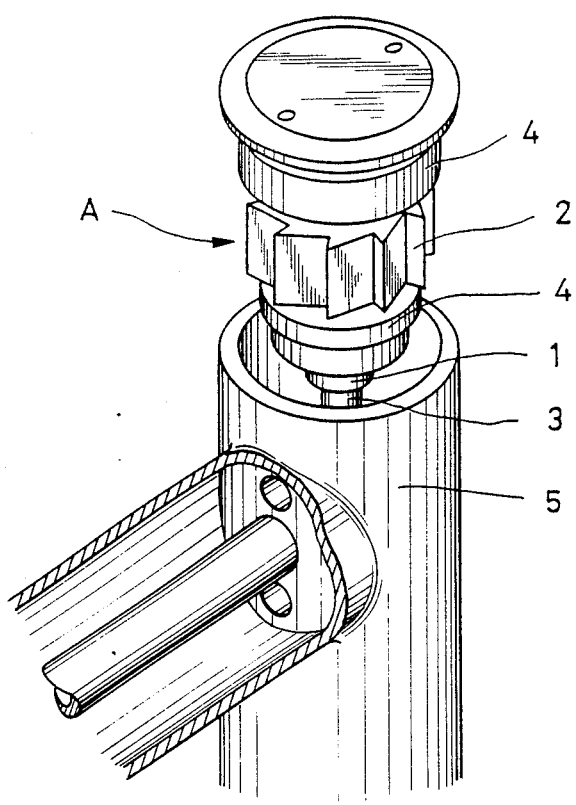
FIG. 1 is a perspective view showing a rotary member which is being mounted in the head of the dental chuckless handpiece according to the present invention.
Figure 4:
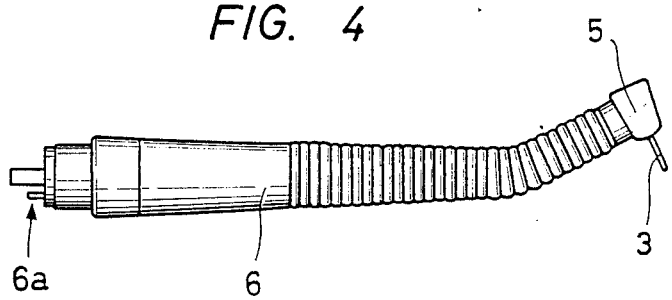
FIG. 4 is a side view of the dental chuckless handpiece according to the present invention.
Figure 5:
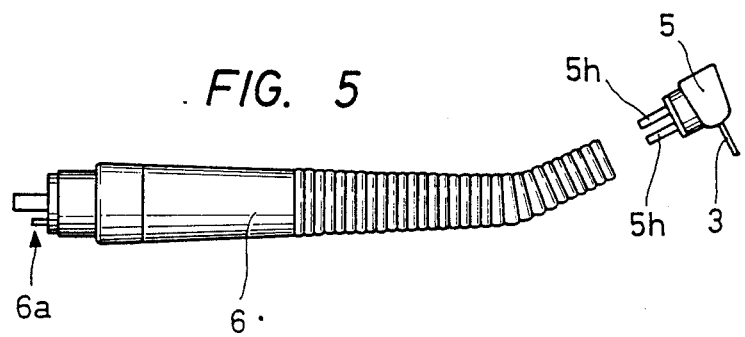
FIG. 5 is a side view of the dental chuckless handpiece according to the present invention, the head of which is detachable.
Figure 6:
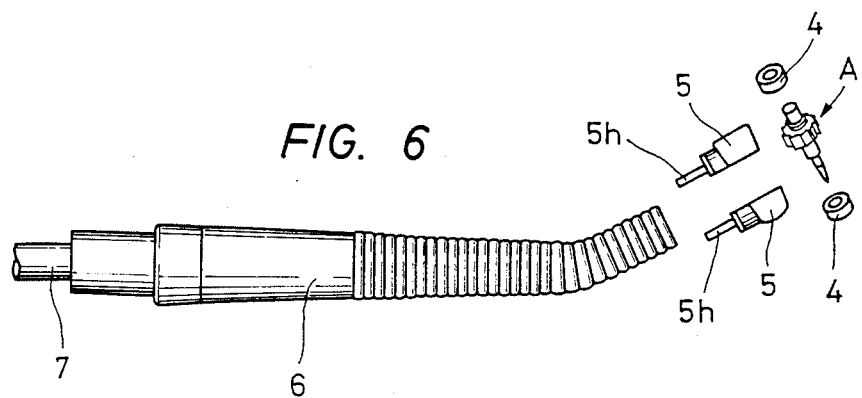
FIG. 6 is a side view illustrating the dental chuckless handpiece of the present invention having a divisible head, in which the bearings are incorporated into the rotary member.

Referring to the drawings, a shaft 1 having a turbine impeller 2 fixedly provided with a cutting tool 3 at its lower end, and bearings 4, 4 are attached to the upper and lower portions of the shaft 1 to define a rotary member A. This rotary member A may be formed in various manners. By way of example, the member A may be formed integrally of a metal material with an NC machine tool or by the precision casting process, or may as a whole be made integrally of an engineering resin such as polysulfone, polyether sulfone or polyphenylene sulfide resin by the precision injection molding process. Alternatively, the shaft 1 having the turbine impeller 2 may be formed integrally of a metal material with an NC machine tool or by the precision casting process or an engineering resin such as polysulfone, polyether sulfone or polyphenylene sulfide resin by the precision injection molding process, and may be fixedly provided with the cutting tool 3 by fitting, brazing or bonding. Still alternatively, the turbine impeller 2, shaft 1 and cutting tool 3 may separately be provided by the aforesaid procedures, the turbine impeller 2 may then be fixed to the shaft 1 by fitting or brazing, and the cutting tool 3 may finally be fixed to the shaft 1 by fitting or brazing. A head 5 of a body 6 of the dental handpiece includes a space 5a provided with a bearing-receiving portion 5b for receiving the bearings 4, 4 attached to the upper and lower portions of the rotary member A. The head 5 includes through its bottom a hole 5c for the provision of the cutting tool 3 fixed to the lower end of the shaft 1 of the rotary member A, and is provided with a compressed air supply path 5d for supplying compressed air to the turbine impeller 2 portion of the rotary member A and a compressed air discharge path 5e for discharging the compressed air used to rotate the turbine impeller 2 and, if required, a chip air supply path 5f and a water supply path 5g. The head 5 may be formed as an integral piece with the dental handpiece body 6; however, it may be designed to be attachable to or detachable from the dental handpiece body 6, as illustrated in FIGS. 5 and 6. Where the head 5 is detachably mounted to the dental handpiece body 6, it may be of the structure that it is divisible along its longitudinal axis. Where the head 5 is designed to be detachably connected to the dental handpiece body 6, it is preferred that they are connected to each other through connecting nozzles 5h, 5h extending from the compressed air supply and exhaust paths 5d and 5e. In the first aspect of the present invention, the dental handpiece body 6 to be used may be formed of brass or stainless steel, as in the prior art. In the second aspect of the present invention, however, it is required that the portions of the body 6 other than the head 5 be formed of a synthetic resin colored in a color including transparent color for the purpose of discrimination and reduction in weight. In the arrangement of this dental handpiece body, the compressed air supply and exhaust paths 5d and 5e provided in the head 5 and the chip air and water supply paths 5f and 5g provided therein, if required, are connected to the associated compressed air supply and exhaust paths and chip air and water supply paths, and the head 5 is provided at its rear end with a connector section 6a for making connections between these paths and a tube 7.

ACTION

The dental chuckless handpiece according to the present invention is of the integral arrangement wherein the rotary member A, that is the most important component of the compressed air drive type dental chuckless handpiece, comprises the shaft 1 having the turbine impeller 2, the cutting tool 3 fixed to the lower end of the shaft 1 and the bearings 4, 4 attached above and below the turbine impeller 2, which generate and maintain high-speed rotation even under load. Thus, since any chuck for the fixation of the cutting tool 3 can be dispensed with, the cutting tool 3 can be fixed in place with no troublesome operation, and noise can be reduced because of limited leakage of compressed air. Further, since the space required for the provision of a chuck for the fixation of the cutting tool 3 can be dispensed with, the size of the head of the handpiece body can be so reduced that it is easy to observe the given regions of the teeth and dentures to be ground. When the cutting tool 3 is inserted and mounted in a chuck portion, there is a fear that since its insertion depth varies in each replacement, the axis of the cutting tool 3 may oscillate or cause co-oscillation. With the present handpiece, however, it is possible to maintain the cutting tool 3 in a stable rotating state. Thus, the operator can manipulate without such fear the present dental chuckless handpiece in which the head 5 is provided with the rotary member A including the cutting tool 3 suitable for the intended purpose and use in the same manner, as is the case with the conventional dental handpiece.

The dental chuckless according to the second aspect of the present invention is provided to solve a grave fatigue problem that arises when the operator manipulates for an extended period the prior art handpiece which is heavy since it is as a whole formed of brass or stainless steel. Since the present handpiece is reduced in weight by forming its body of a synthetic resin in such a manner that at least the portions of the body except its head are made partly transparent and partly colored so as to correspond the type of cutting tool to the color in one-match-one relation. It is thus easy to discriminate, select and employ the present dental chuckless handpiece in which the head 5 is provided with the rotary member A including the cutting tool 3 suitable for the intended purpose and use. Where the head 5 is formed of a transparent synthetic resin, it is also possible to ascertain the lubrication of the bearings 4 and the operation of the rotary member A.

EFFECT OF THE INVENTION

As detailed above, the dental chuckless handpiece according to the present invention is of the integral arrangement wherein the rotary member A, that is the most important component of the compressed air drive type dental chuckless handpiece, comprises the shaft 1 having the turbine impeller 2, the cutting tool 3 fixed to the lower end of the shaft 1 and the bearings 4, 4 attached above and below the turbine impeller 2, which generate and maintain high-speed rotation even under load. Thus, the number of the components involved is reduced to a minimum, whereby the production cost is cut down. Any chuck for the fixation of the cutting tool 3 can be dispensed with, whereby the cutting tool 3 can be fixed in place with no troublesome operation, and noise can be reduced because of limited leakage of compressed air. In addition, the space required for the provision of a chuck for the fixation of the cutting tool 3 can be dispensed with, whereby the size of the head of the handpiece body can also be reduced making it easy to observe the given regions of the teeth and dentures to be ground. Moreover, since it is possible to maintain the cutting tool 3 in a stable rotating state free from the oscillation of the axis of the cutting tool or co-oscillation, the operator can manipulate the present handpiece without any fear.

The dental chuckless handpiece according to the second aspect of the present invention is provided to solve a grave fatigue problem that arises when the operator manipulates for an extended period the prior art handpiece which is heavy because it is formed as a whole of brass or stainless steel. That problem can be solved by forming at least the portions of the body 6 except its head 5 of a synthetic resin, and the difficulty in discrimination of the cutting tool 3 fixed to the rotary member A due to the fact that replacement of the cutting tool 3 is not easy or unfeasible because the aforesaid integral rotary member A having the bearings 4, 4 attached to the upper an lower portions of the shaft 1 is mounted in the head 5 can be eliminated by coloring at least the portions with a color including transparency for the purpose of corresponding the type of cutting tool to that color in one-match-one relation, thereby affording discriminability to said handpiece. Such weight reductions and easy discriminability make it possible for the operator to easily manipulate the handpiece for an extended period without fear and fatigue. Moreover, where the head 5 is formed of a transparent synthetic resin, it is possible to ascertain whether or not the bearings 4, 4 are entirely lubricated and detect malfunctions of the rotary member A during operation.

The dental chuckless handpiece according to the present invention having various advantages as mentioned above make a great contribution to dentistry.

What is claimed is:

1. A dental chuckless handpiece of the compressed air drive type, including a body having a head in which bearings are attached to the upper and lower portions of a shaft provided with a turbine impeller, and a rotary member having a cutting tool fixedly provided to the lower end of said shaft is mounted in place through said upper and lower bearings;
    at least portions of said body excepting said head being formed of a synthetic resin discriminably colored with a color including transparent color.

2. A handpiece as defined in claim 1, wherein said rotary member is detachably mounted in said head.

3. A handpiece as defined in claim 1 or 2, wherein said head having said rotary member mounted therein is removably attached to said body.

4. A handpiece as defined in claim 3, wherein said rotary member comprises an integral piece of said shaft having said turbine impeller and said cutting tool.

5. A handpiece as defined claim 3, wherein said rotary member comprises said shaft having said turbine impeller, and said cutting tool which is formed separately therefrom and fixed thereto.

6. A handpiece as defined claim 3, wherein said rotary member comprises said turbine impeller, said shaft and said cutting tool which are formed separately from each other and fixed to each other.

* * * * *